United States Patent [19]

Knifton et al.

[11] Patent Number: 4,622,343

[45] Date of Patent: Nov. 11, 1986

[54] PROCESS FOR C₁-C₄ ALKANOL PRODUCTION FROM SYNTHESIS GAS USING A TRIMETALLIC CATALYST

[75] Inventors: John F. Knifton; Neal J. Grice, both of Austin, Tex.

[73] Assignee: Texaco Inc., White Plains, N.Y.

[21] Appl. No.: 801,261

[22] Filed: Nov. 25, 1985

[51] Int. Cl.⁴ .................................................. C07C 27/06
[52] U.S. Cl. ........................................ 518/700; 512/155
[58] Field of Search .............................................. 518/700

[56] References Cited

U.S. PATENT DOCUMENTS 4,332,915  6/1982  Knifton ................................ 518/200
4,396,726  8/1983  Simons ................................ 518/200

Primary Examiner—Howard T. Mars
Attorney, Agent, or Firm—Jack H. Park; Kenneth R. Priem; Cynthia L. Kendrick

[57] ABSTRACT

This invention concerns a process for making $C_1$-$C_4$ alkanols and particularly ethanol which comprises contacting a mixture of CO and $H_2$ at a pressure of 30 atm or greater and at a temperature of at least 150° C. with a catalyst system comprising a ruthenium-containing compound, a cobalt-containing compound and a manganese-containing compound dispersed in a low melting quaternary phosphonium salt.

19 Claims, 6 Drawing Figures

Octane enhancer synthesis ratios with Ru=1 and Co=2 function of (Mn)

Productivity for OES RuCo12a function of (Mn)

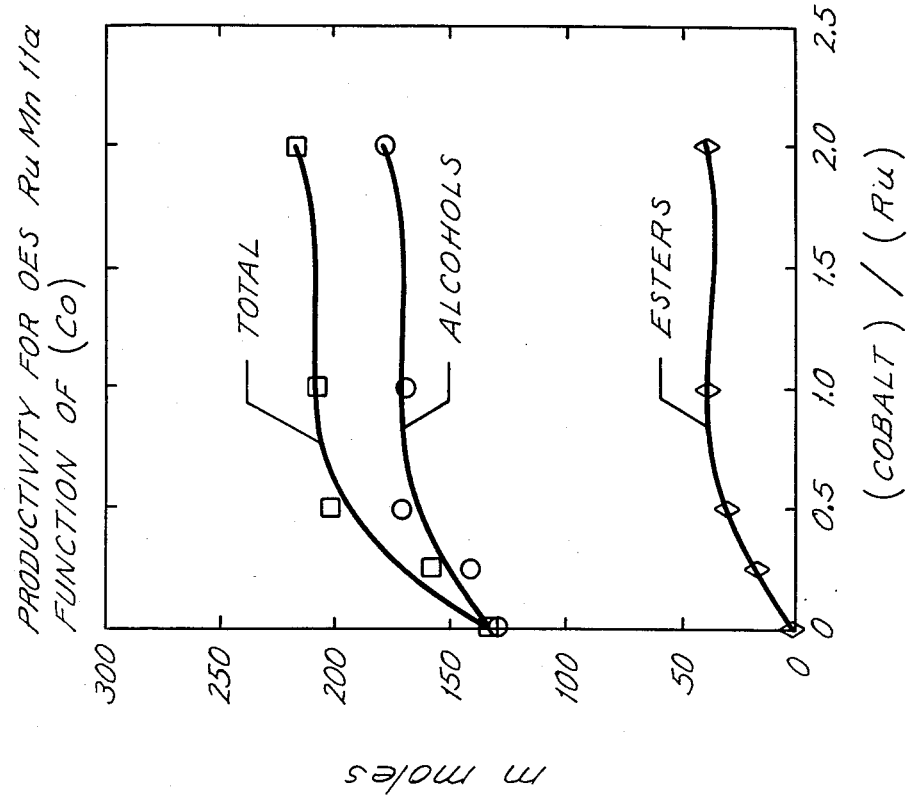
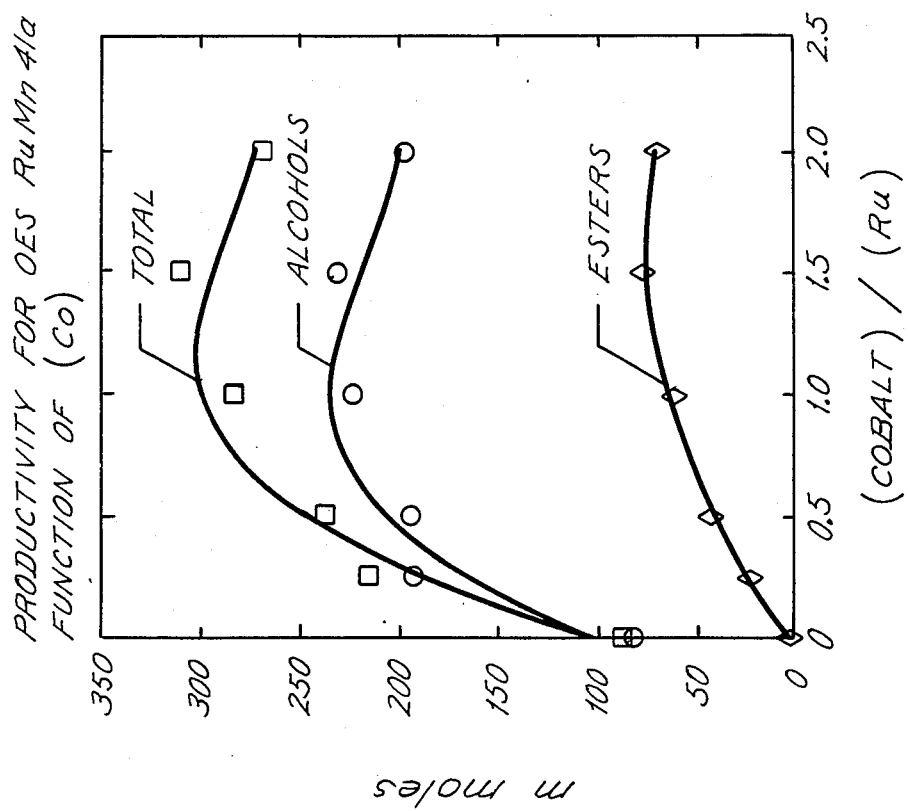

PROCESS FOR $C_1$-$C_4$ ALKANOL PRODUCTION FROM SYNTHESIS GAS USING A TRIMETALLIC CATALYST

BACKGROUND OF THE INVENTION

1. Field of the Invention

This invention concerns an improved process for preparing $C_1$-$C_4$ alkanols from synthesis gas with a trimetallic 'melt' catalyst. There is an improvement in total $C_1$-$C_4$ alcohol + $C_1$-$C_4$ alkyl acetate productivity, an improvement in $C_1$-$C_4$ alcohol productivity, an improvement in ethanol productivity, and an improvement in total $C_1$-$C_4$ alcohol to $C_1$-$C_4$ alkyl acetates molar ratio.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C. or more using as a catalyst a mixture of copper, chromium and zinc oxides. A wide variety of other catalysts have been employed in the reaction of carbon monoxide and hydrogen to yield liquid products containing substantial amounts of monofunctional alcohols as exemplified by methanol, ethanol, propanol, etc.

In U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese, the product formed contains substantial amounts of ethanol and in U.S. Pat. No. 4,197,253, where the reaction of carbon monoxide and hydrogen is conducted in the presence of a rhodium carbonyl complex and a phosphine oxide compound, the resulting product contains a high concentration of methanol. Likewise, when the same reactants are contacted with a rhodium carbonyl complex and a copper salt a liquid product containing a substantial amount of methanol is formed.

U.S. Pat. No. 4,332,915 teaches a process of making alkanols, and particularly ethanol, using a catalyst comprising a ruthenium-containing compound and a cobalt-containing compound dispersed in a low melting quaternary phosphonium or ammonium salt.

U.S. Pat. No. 4,332,914 also discloses a process for making alkanols, but with a greater proportion of methanol, using a ruthenium and halogen-free rhenium or manganese compound dispersed in a low melting quaternary salt or base.

A similar catalyst system is used in U.S. Pat. No. 4,362,821, except an inert oxygenated solvent is used. Again, the primary product is methanol.

In cases where bimetallic catalysts are used, it is noted that a ruthenium-containing compound can be used with a second metal comprising nickel or iron, samarium or a Group IVB, VB or VIB containing compound wherein both metals are dispersed in a quaternary phosphonium salt to produce good yields of methanol and ethanol along with some propanol, butanol and esters. See U.S. Pat. Nos. 4,436,837; 4,436,838; and 4,434,248.

None of these references suggests or teaches a trimetallic catalyst which exhibits improved productivity, improved alcohol/ester ratio, improved productivity of total oxygenates, and improved ethyl/methyl ratios.

The discovery of a process exhibiting improved productivity for $C_1$-$C_4$ alcohols plus $C_1$-$C_4$ alkyl acetates using a unique trimetallic catalyst system would be an advance in the art.

SUMMARY OF THE INVENTION

This invention concerns a method for making $C_1$-$C_4$ alkanols which comprises contacting a mixture of CO and $H_2$ at a pressure of 30 atm or greater and at a temperature of at least 150° C. with a trimetallic catalyst system comprising a ruthenium-containing compound, a cobalt-containing compound and a manganese-containing compound dispersed in a low melting quaternary phosphonium salt wherein there is improved productivity in total $C_1$-$C_4$ alcohol + $C_1$-$C_4$ alkyl acetates, an improved $C_1$-$C_4$ alcohol production, improved ethanol productivity, and improved $C_1$-$C_4$ alcohol to $C_1$-$C_4$ alkyl acetate molar ratio.

BRIEF DESCRIPTION OF THE DRAWINGS

FIG. 5 illustrates the effect of varying the moles of cobalt compound in the catalyst.

FIG. 6 illustrates the effects of varying the moles of cobalt when more manganese is used.

DETAILED DESCRIPTION OF THE INVENTION

Figure 2:
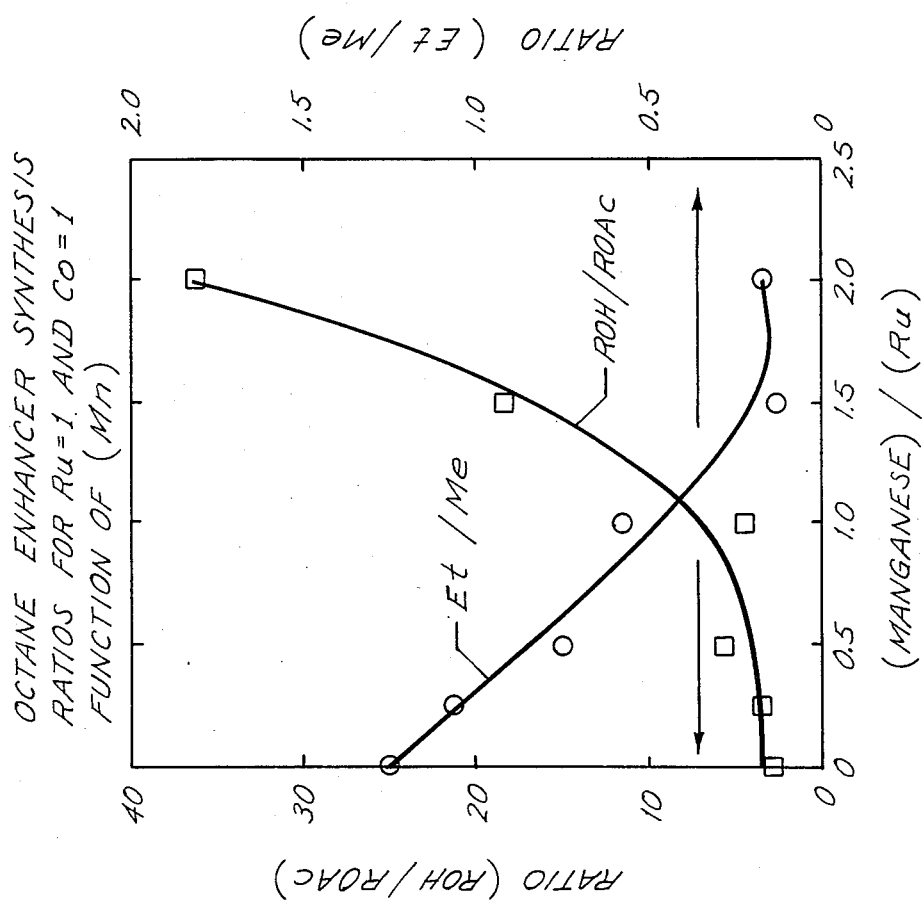
FIG. 2 illustrates the $C_1$-$C_4$ alcohol/$C_1$-$C_4$ alkyl acetate molar ratio and total ethyl groups to total methyl groups.

In the narrower and more preferred practice of this invention $C_1$-$C_4$ oxygenates, with an improved alcohol to acetate ratio are prepared by contacting a mixture of CO and $H_2$ at a temperature of about 180° to about 250° C. and at a pressure of 130 atm to 600 atm or greater, with a catalyst system comprising one or more ruthenium-containing compounds, one or more cobalt-containing compounds and one or more manganese-containing compounds dispersed in a low melting quaternary phosphonium base wherein there is improved productivity in total $C_1$-$C_4$ alcohol + $C_1$-$C_4$ alkyl acetate, an improved $C_1$-$C_4$ alcohol production, improved ethanol productivity, and improved $C_1$-$C_4$ alcohol to $C_1$-$C_4$ alkyl acetate molar ratio.

The reaction can be represented by the equation:

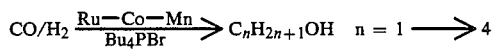

$$CO/H_2 \xrightarrow[Bu_4PBr]{Ru-Co-Mn} C_nH_{2n+1}OH \quad n = 1 \longrightarrow 4$$

As previously pointed out the catalyst system employed in the practice of this invention contains one or more ruthenium-containing compounds, one or more cobalt-containing compounds and one or more manganese-containing compounds. The ruthenium-containing catalyst as well as the cobalt-containing catalyst and manganese-containing catalyst may be chosen from a wide variety of organic or inorganic compounds, complexes, etc., as will be shown and illustrated below. It is only necessary that the catalyst precursor actually employed contain the metals in any of their ionic states. The actual catalytically active species is then believed to comprise ruthenium, cobalt and manganese in complex combination with the quaternary salt, promoter and with carbon monoxide and hydrogen. The most effective catalysis is believed to be achieved where a ruthenium carbonyl, cobalt hydrocarbonyl and manganese carbonyl species are solubilized in a quaternary phosphonium salt under reaction conditions.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The cobalt-containing catalyst precursors may take many different forms. For instance, the cobalt may be added to the reaction mixture in an oxide form, as in the case of, for example, cobalt(II) oxide (CoO) or cobalt(II,III) oxide ($Co_3O_4$). Alternatively, it may be added as the salt of a mineral acid, as in the case of cobalt(II) nitrate, hydrate ($Co(NO_3)_2.6H_2O$), cobalt(II) sulphate, etc., or as the salt of a suitable organic carboxylic acid, for example, cobalt(II) formate, cobalt(II) acetate, cobalt(II) propionate, cobalt(II) oxalate, cobalt naphthenate, as well as cobalt complexes with carbonyl-containing ligands as in the case of cobalt(II) acetylacetonate and cobalt(III) acetylacetonates, etc. The cobalt may also be added to the reaction zone as cobalt carbide, cobalt(II) carbonate and a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenyl phosphine cobalt tricarbonyl dimer, etc.

Preferred cobalt-containing compounds include oxides of cobalt, cobalt salts of organic carboxylic acids and cobalt carbonyl or hydrocarbonyl derivatives. Among these, particularly preferred are cobalt(II) acetylacetonate, cobalt(III) acetylacetonate, cobalt(II) acetate, cobalt(II) propionate, and dicobalt octacarbonyl.

The manganese catalyst precursors may take different forms. For instance, the manganese may be added to the reaction mixture in an oxide form, as in the case of, for example, of manganese(IV) oxide, manganese(III) oxide and manganese(VI) oxide. Alternatively, it may be added as salt of a mineral acid, as in the case of manganese(II) nitrate and manganese(II) sulfate, and as the salt of a suitable organic carboxylic acid such as, for example, manganese(II) acetate, manganese(III) acetate and manganese oxalate, or as the complex of a carbonyl-containing ligand, as in the case of manganese(II) acetylacetonate or manganese(III) acetylacetonate, etc. Manganese carbide, carbonate, carbonyl, halide and hydrocarbonyl derivatives such as manganese carbide, manganese(II) carbonate, manganese(II) chloride, manganese(II) bromide and dimanganese decacarbonyl are also effective catalyst precursors.

Preferred manganese-containing compounds include carbonates such as manganese(II) carbonate, complexes of carbonyl-containing ligand such as manganese(III) acetylacetonate manganese carbonyls such as dimanganese decacarbonyl as well as salts of organic acids such as manganese(II) acetate.

The ruthenium, cobalt and manganese-containing compounds are, prior to their catalytic use in making alkanols, first dispersed in a low melting quaternary phosphonium salt. It is interesting to note that the ruthenium-containing compound alone, without being dispersed in said salt, has little, if any activity in promoting the manufacture of alkanols from synthesis gas. In addition, the ruthenium and cobalt-containing compounds alone, without the manganese produce less total oxygenates and a lower ratio of $C_1$–$C_4$ alkanols to $C_1$–$C_4$ alkyl acetates.

The quaternary phosphonium salt must be relatively low melting, that is, melt at a temperature less than about the temperature of reaction of making alkanols. Usually the quaternary compound has a melting point less than about 180° C., and most often has a melting point less than 150° C.

Suitable quaternary phosphonium salts have the formula:

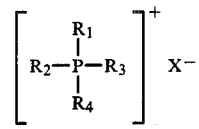

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium chromate, tetrabutylphosphonium tetrafluoroborate and tetrabutylphosphonium acetate. The examples cited here provide evidence of the effectiveness of the quaternary phosphonium salts when in combination with triruthenium dodecacarbonyl.

The preferred quaternary salts are generally the tetralkylphosphonium salts containing alkyl groups having 1-6 carbon atoms, such as methyl, ethyl and butyl. Tetrabutylphosphonium salts, such as tetrabutylphosphonium bromide, are most preferred for the practice of this invention.

Preferred tetrabutylphosphonium salts include the bromide, chloride, iodide, acetate and chromate salts.

Generally, in the catalyst system the molar ratio of the ruthenium compound, cobalt compound or manganese compound to the quaternary phosphonium salt will range from about 1:0.01 to about 1:100 or more and, preferably, will be from about 1:0.5 to about 1:20.

The quantity of ruthenium compound, cobalt compound and manganese compound employed in the instant invention is not critical and may vary over a wide range. In general, the novel process is desirably conducted in the presence of a catalytically effective quantity of the active ruthenium species, cobalt species and manganese species which gives the desired product in reasonable yield. The reaction proceeds when employing as little as about $1 \times 10^{-6}$ weight percent, and even lesser amounts of ruthenium together with about $1 \times 10^{-6}$ weight percent or less of cobalt and $1 \times 10^{-6}$ weight percent of manganese, basis the weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a cobalt concentration of from about $1 \times 10^{-5}$ to about 5 weight percent and a manganese concentration of from about $1 \times 10^{-5}$ to ca. 5 percent based on the total weight of reaction mixture is generally desirable in the practice of this invention. The preferred ruthenium-to-cobalt-to-manganese atomic ratio is from 10:1:0.1 to 1:10:100.

Maximum total $C_1$–$C_4$ alcohol productivity is reached with an initial Ru:Co:Mn ratio of 1:1.5:0.25. This is illustrated by data in FIG. 5.

The temperature range which can usefully be employed in these syntheses is a variable dependent upon other experimental factors, including the pressure, and the concentration and choice of the particular species of ruthenium catalyst among other things. The range of operability is from about 150° C. to 350° C. when superatmospheric pressure of syngas are employed. A narrow range of 180° to 250° C. represents the preferred temperature range.

Superatmospheric pressures of 30 atm or greater lead to substantial yields of alkanols by the process of this invention. A preferred operating range is from 130 atm to 600 atm, although pressures above 600 atm also provide useful yields of the desired alkanols.

The relative amounts of carbon monoxide and hydrogen which may be initially present in the syngas, i.e., synthesis gas, mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxylic acids may also be formed during the course of this desired alkanol synthesis. Most often these are $C_1$–$C_4$ alkyl ester derivatives of acetic acid such as methyl acetate, ethyl acetate, propyl acetate, which can be conveniently recovered from the reaction mixture. The advantage of this process is an improvement in the total selectivity to $C_1$–$C_4$ alcohols plus $C_1$–$C_4$ alkyl acetates, improved $C_1$–$C_4$ alcohol productivity, improved ethanol productivity and improved ratio of $C_1$–$C_4$ alkanols to $C_1$–$C_4$ alkyl acetates. These improvements are illustrated in Example 1 versus comparative Examples A and B. The increase in the $C_1$–$C_4$ alcohol/$C_1$–$C_4$ alkyl acetate molar ratio is by a factor of 12-15. This is illustrated by the data in FIGS. 2 and 4. With, for example, the $Ru_3(CO)_{12}$—$Co_2(CO)_8Mn_2(CO)_{10}$ catalyst combination dispersed in $Bu_4PBr$, total $C_1$–$C_4$ oxygenates may comprise up to 99 wt % of the total liquid product, $C_1$–$C_4$ alkanols may comprise 95 wt % and the ratio of $C_1$–$C_4$ alkanols to $C_1$–$C_4$ alkyl acetates may be as high as 40 or more.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ethanol rich product, and said material may be recovered by methods well known in the art, such as distillation, fractionation, extraction and the like. A fraction rich in the ruthenium and cobalt catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been in parts by weight; all temperatures are in degrees centigrade and all pressures in atmospheres (atm).

Various embodiments of the process of this invention are illustrated in the following examples which are to be considered not limitative.

EXAMPLE I

A mixture of ruthenium dodecacarbonyl (0.85 g, 4.0 mmole Ru), cobalt octacarbonyl (0.68 g, 4.0 mmole Co) and manganese decacarbonyl (0.39 g, 2.0 mmole Mn)

dispersed in tetrabutylphosphonium bromide (15.0 g) is transferred in a glass liner under $N_2$ purge, to an 850 ml capacity pressure reactor equipped with heating and means of agitation. The reactor is sealed, flushed with $CO/H_2$ (1:1) and pressured to 136 atm. with $CO/H_2$ (1:1). The mixture is heated to 230° C. with rocking, the pressure raised to 238 atm by $CO/H_2$ addition from a large surge tank, and the reactor held at temperature for 6 hours. Pressure in the reactor is maintained at ca. 238 atm by incremental additions of $CO/H_2$ from the surge tank.

On cooling, the reactor pressure (142 atm) is noted, a typical gas sample taken, and the excess gas removed. The reddish-brown liquid product (31.2 g) is analyzed by glc and Karl-Fischer titration.

Typical data for the liquid product are as follows:
27.5 wt % methanol
27.5 wt % ethanol
6.8 wt % propanols
0.1 wt % butanols
8.5 wt % methyl acetate
12.4 wt % ethyl acetate
2.6 wt % propyl acetates
0.6 wt % butyl acetates The liquid yield increase is 31.2 g−16.9 g=14.3 g
Estimated productivity of each alcohol and ester fraction is:
123 mmole methanol
85 mmole ethanol
16 mmole propanols
0.2 mmole butanols
16 mmole methyl acetate
20 mmole ethyl acetate
3.6 mmole propyl acetates
0.7 mmole butyl acetates
Total $C_1$-$C_4$ alcohol productivity is 224 mmoles.
Total $C_1$-$C_4$ alkyl acetate productivity is 40 mmoles.
Total $C_1$-$C_4$ alcohol/total $C_1$-$C_4$ alkyl acetate molar ratio is 224/40=5.6.
Total $C_1$-$C_4$ alcohol + $C_1$-$C_4$ alkyl acetate productivity is 264 mmoles.

COMPARATIVE EXAMPLE A

This comparative example illustrates the effect upon $C_1$-$C_4$ alcohol productivity and $C_1$-$C_4$ alcohol/$C_1$-$C_4$ acetate ratio of using the ruthenium carbonyl-cobalt carbonyl/tetrabutylphosphonium bromide catalyst with no manganese component.

A mixture of ruthenium dodecacarbonyl (0.85 g, 4.0 mmole Ru) and cobalt octacarbonyl (0.68 g, 4.0 mmole Co) dispersed in tetrabutylphosphonium bromide (15.0 g) is transferred in a glass liner under $N_2$ purge, to the 850 ml capacity pressure reactor of Example I. The reactor is sealed, flushed with $CO/H_2$ and pressured to 136 atm with $CO/H_2$ (1:1). The mixture is heated to 230° C. with rocking, the pressure raised to 238 atm by $CO/H_2$ addition from a large surge tank, and the reactor held at temperature for 6 hours as in Example I.

On cooling, a typical gas sample is taken, the excess gas removed, and the reddish-brown liquid product (31.5 g) is analyzed by glc.

Typical data for the liquid product are as follows:
17.2 wt % methanol
26.1 wt % ethanol
10.1 wt % propanols
7.7 wt % methyl acetate
20.4 wt % propyl acetate
7.2 wt % propyl acetates
1.7 wt % butyl acetates The liquid yield increase is 31.2 g−16.5 g=15.0 g
Estimated productivity of each alcohol and ester fraction is:
80 mmole methanol
85 mmole ethanol
25 mmole propanols
1.0 mmole butanols
16 mmole methyl acetate
35 mmole ethyl acetate
11 mmole propyl acetates
2.2 mmole butyl acetates
Total $C_1$-$C_4$ alcohol productivity is 191 mmoles.
Total $C_1$-$C_4$ alkyl acetate productivity is 64 mmoles.
Total $C_1$-$C_4$ alcohol/total $C_1$-$C_4$ alkyl acetate molar ratio is 191/64=3.0.
Total $C_1$-$C_4$ alcohol + $C_1$-$C_4$ alkyl acetate productivity is 255 mmoles.

In this example it may be noted that both the total $C_1$-$C_4$ alcohol productivity and the $C_1$-$C_4$ alcohol/$C_1$-$C_4$ alkyl acetate molar ratios are significantly lower than in Example I.

COMPARATIVE EXAMPLE B

This comparative example illustrates the effect upon $C_1$-$C_4$ alcohol productivity and $C_1$-$C_4$ alcohol/$C_1$-$C_4$ alkyl acetate ratio of using the ruthenium-manganese carbonyl/tetrabutylphosphonium bromide catalyst with no cobalt component.

A mixture of ruthenium dodecacarbonyl (0.85 g, 4.0 mmole Ru) and manganese decacarbonyl (0.39 g, 2.0 mmole Mn) dispersed in tetrabutylphosphonium bromide (15.0 g) is transferred in a glass liner under $N_2$ purge, to the 850 ml capacity pressure reactor of Example 1. The reactor is sealed, flushed with $CO/H_2$ and pressured to 136 atm with $CO/H_2$ (1:1). The mixture is heated to 230° C. with rocking, the pressure raised to 238 atm by $CO/H_2$ addition from a large surge tank and the reactor held at temperature for 6 hours as in Example 1.

On cooling, a typical gas sample is taken, the excess gas removed and the reddish-brown liquid product (20.9 g) is analyzed by glc.

Typical data for the liquid product are as follows:
66.7 wt % methanol
14.7 wt % ethanol
0.5 wt % propanols
0.4 wt % butanols
1.9 wt % methyl acetate
1.7 wt % ethyl acetate
0.6 wt % butyl acetates The liquid yield increase is 20.9 g−16.2 g=4.7 g.
Estimated productivity of each alcohol and ester fraction is:
98 mmole methanol
15 mmole ethanol
0.4 mmole propanols
0.3 mmole butanols
1.2 mmole methyl acetate
0.9 mmole ethyl acetate
0.2 mmole butyl acetates
Total $C_1$-$C_4$ alcohol productivity is 114 mmoles.
Total $C_1$-$C_4$ alkyl acetate productivity is 2.3 mmoles.
Total $C_1$-$C_4$ alcohol/total $C_1$-$C_4$ alkyl acetate molar ratio is 114/2.3=50
Total $C_1$-$C_4$ alcohol + $C_1$-$C_4$ alkyl acetate productivity is 116 mmoles.

In this example it may be seen that the total $C_1$–$C_4$ alcohol productivity, the ethanol productivity and the $C_1$–$C_4$ alkyl acetate productivity are significantly lower than in Example I and that the alkanol fraction is predominantly methanol.

EXAMPLES 2-6

In these examples, following the procedure of Example 1, the reactor is charged with:
 ruthenium dodecacarbonyl (4.0 mmole Ru)
 Cobalt octacarbonyl (4.0 mmole Co)
Varying quantities of manganese decacarbonyl, including zero, 1.0 mmole, 4.0 mmole, 6.0 mmole, and 8.0 mmole Mn were used in the tetrabutylphosphonium bromide (15.0 g).

Figure 1:
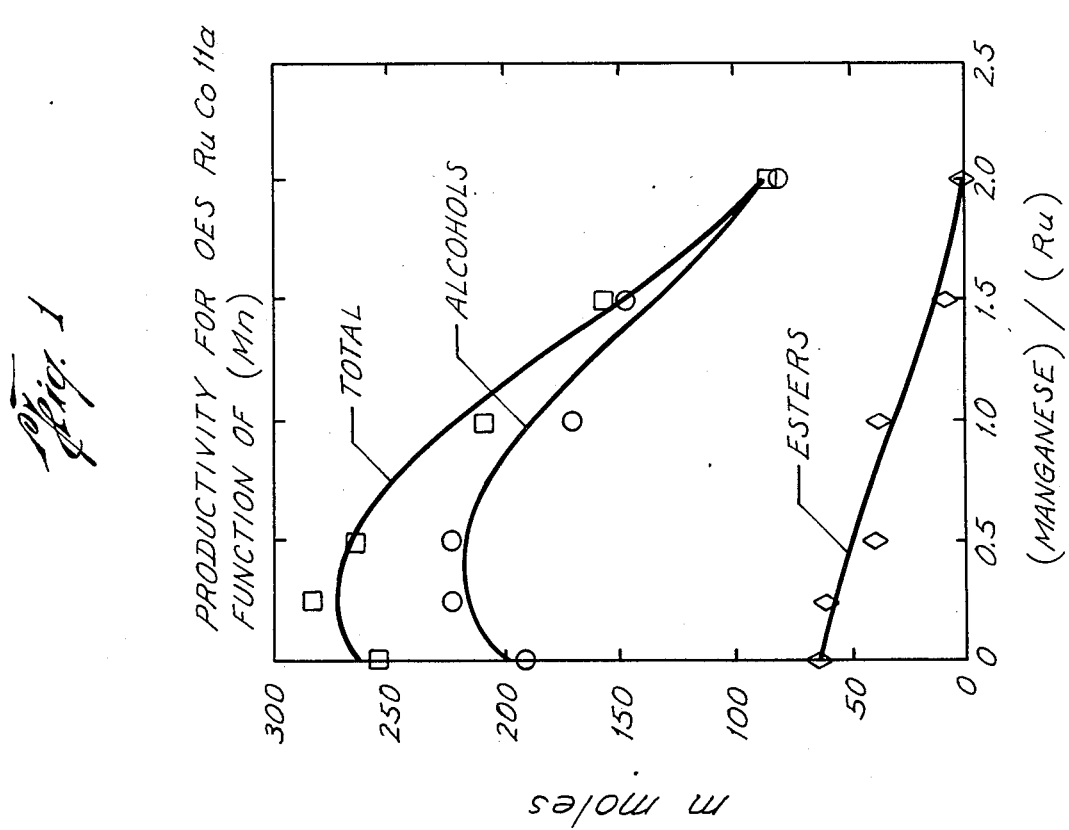
FIG. 1 demonstrates the effect upon product composition caused by changes in manganese decacarbonyl content.

The effect these changes in manganese decacarbonyl content had upon the product composition is illustrated in FIG. 1.
 Total $C_1$–$C_4$ alcohol + $C_1$–$C_4$ alkyl acetate is represented by □,
 total $C_1$–$C_4$ alcohol is represented by ◯, and
 total $C_1$–$C_4$ alkyl acetate is represented by ◊.
 Also, $C_1$–$C_4$ alcohol/$C_1$–$C_4$ alkyl acetate molar ratio, (□ ) and total ethyl groups to total methyl groups, ( ) is illustrated in the accompanying FIG. 2.

It may be noted from these figures that:
1. The introduction of manganese increases the total alcohol plus alkyl acetate productivity and the total $C_1$–$C_4$ alcohol productivity. In FIG. 1 the maximum alcohol + alkyl acetate productivity is achieved at an initial molar ratio of Ru:Co:Mn of 1:1:0.25.
2. The introduction of manganese substantially increases the $C_1$–$C_4$ alcohol/$C_1$–$C_4$ alkyl acetate molar ratio by a factor of twelve (from 3.0 at zero Mn, to 36 at 8.0 mmole Mn, see FIG. 2).

EXAMPLES 7-12

In these examples, following the procedure of Example 1, the reactor is charged with:
 ruthenium dodecacarbonyl (4.0 mmole Ru),
 cobalt octacarbonyl (8.0 mmole Co),
varying quantities of manganese decacarbonyl, including zero, 1.0 mmole, 2.0 mmole, and 4.0 mmole, 6.0 mmole and 8.0 mmole Mn plus tetrabutylphosphonium bromide (15.0 g).

Figure 3:
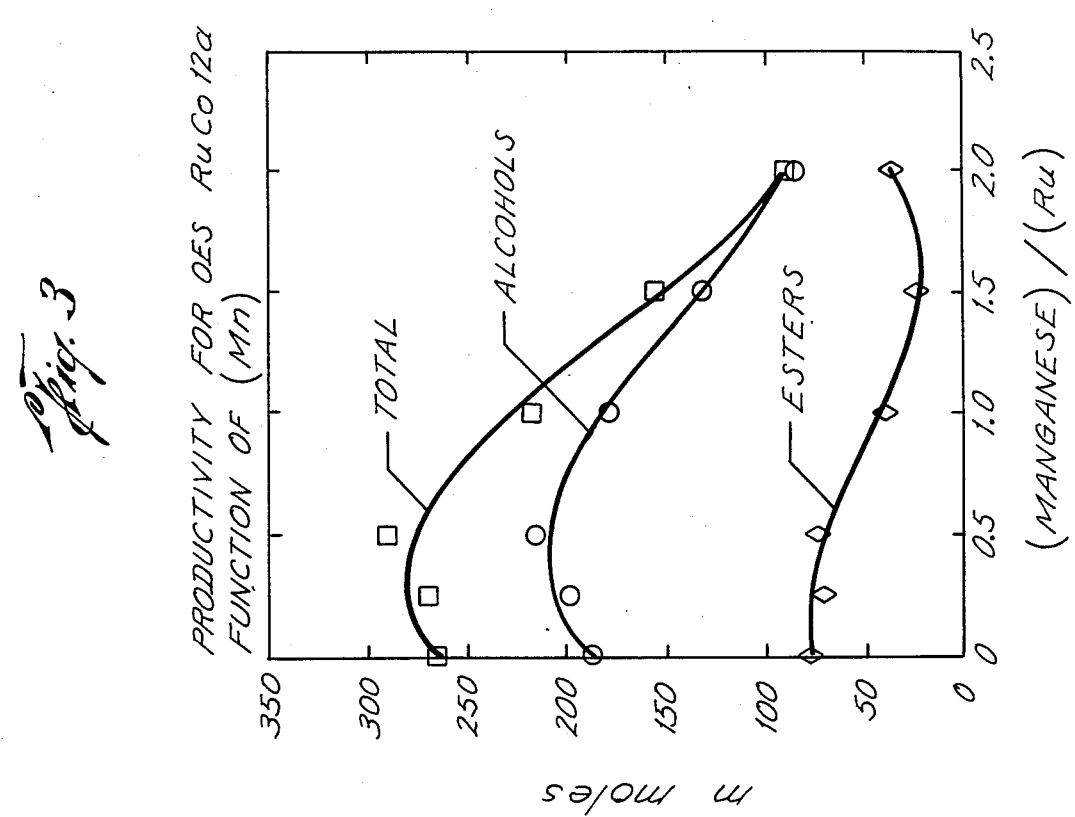
FIG. 3 illustrates the total alcohol plus alkyl acetate productivity, the total $C_1$-$C_4$ alcohol productivity, and the total $C_1$-$C_4$ alkyl acetate productivity, where the amount of cobalt compound is larger and the moles of manganese is varied.

The effect of these changes in manganese decacarbonyl content upon the product composition is illustrated by FIG. 3.
 Total $C_1$–$C_4$ alcohol + $C_1$–$C_4$ alkyl acetate is represented by □,
 total $C_1$–$C_4$ alcohol is represented by ◯, and total $C_1$–$C_4$ alkyl acetate is represented by ◊.
 $C_1$–$C_4$ alcohol/$C_1$–$C_4$ alkyl acetate molar ratio and total ethyl groups/total methyl groups is illustrated in the accompanying FIG. 4.

Figure 4:
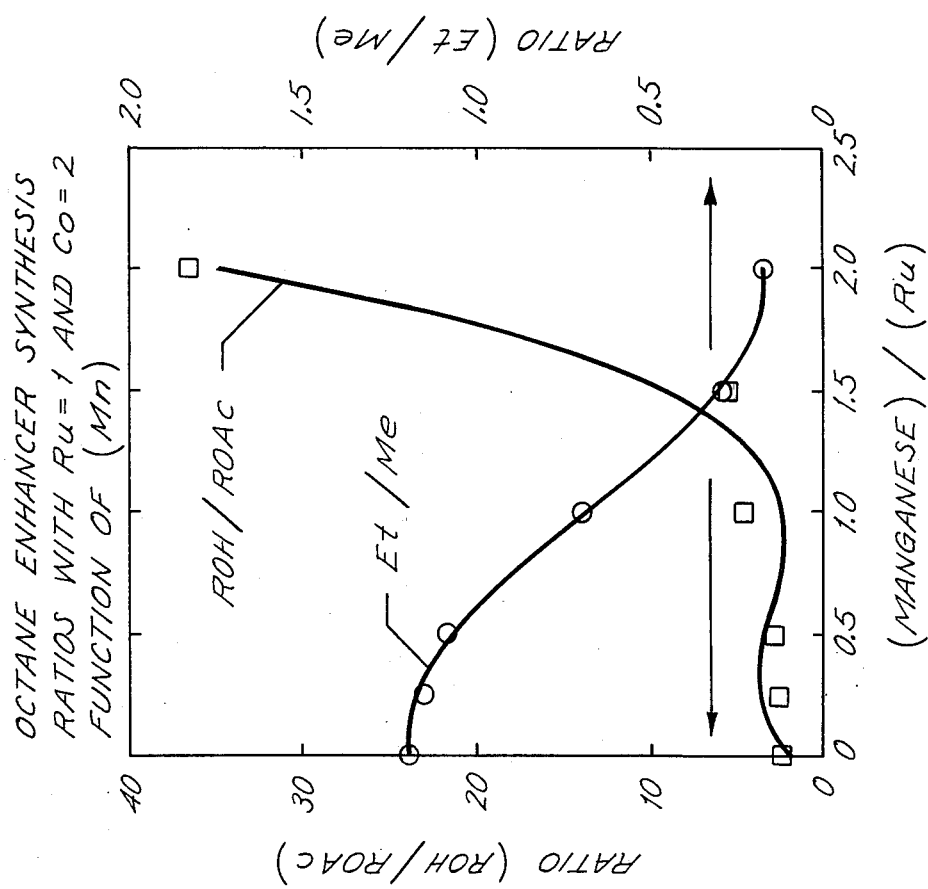
FIG. 4 illustrates how the introduction of manganese substantially increases the $C_1$-$C_4$ alcohol/$C_1$-$C_4$ alkyl acetate molar ratio.

It may be noted from these figures that:
1. The introduction of manganese increases the total alcohol plus alkyl acetate productivity and the total $C_1$–$C_4$ alcohol productivity. The maximum alcohol + alkyl acetate productivity is achieved at an initial molar ratio of Ru:Co:Mn of 1:2.0:0.5 as shown in FIG. 3.
2. The introduction of manganese substantially increases the $C_1$–$C_4$ alcohol/$C_1$–$C_4$ alkyl acetate molar ratio by a factor of fifteen (from 2.4 at zero Mn to 37 at 8.0 mmole Mn) as shown in FIG. 4.

EXAMPLES 13-18

In these examples, following the procedure of Example 1, the reactor is charged with:
 ruthenium dodecacarbonyl (4.0 mmole Ru)
 manganese decacarbonyl (1.0 mmole Mn),
varying quantities of cobalt octacarbonyl, including zero, 1.0 mmole, 2.0 mmole, 4.0 mmole, 6.0 mmole and 8.0 mmole Co., and
 tetrabutylphosphonium bromide (15.0 g).

The effect of these changes in cobalt octacarbonyl content upon the product composition, is illustrated in FIG. 5.
 Total $C_1$–$C_4$ alcohol + $C_1$–$C_4$ alkyl acetate is represented by □,
 total $C_1$–$C_4$ alcohol is represented by ◯, and total $C_1$–$C_4$ alkyl acetate is reprsented by ◊.

It may be noted from these figures that the introduction of cobalt to the ruthenium-manganese catalyst, substantially increases the total alcohol + alkyl acetate productivity and the total $C_1$–$C_4$ alcohol productivity. The maximum alcohol + alkyl acetate productivity is achieved at an initial Ru:Co:Mn molar ratio, in this case, of 1:1.5:0.25.

EXAMPLES 19-23

In these examples, the procedure of Example I was followed and the reactor is charged with:
 ruthenium dodecacarbonyl (4.0 mmole Ru),
 manganese decacarbonyl (4.0 mmole Mn),
varying quantities of cobalt octacarbonyl, including zero, 1.0 mmole, 2.0 mmole, 4.0 mmole, and 8.0 mmole Co. and
 tetrabutylphosphonium bromide (15.0 g).

The effect of these changes in cobalt octacarbonyl content upon the product composition, particularly is illustrated in the accompanying FIG. 6.
 Total $C_1$–$C_4$ alcohol + $C_1$–$C_4$ alkyl acetate = □.
 Total $C_1$–$C_4$ alcohol = ◯.
 Total $C_1$–$C_4$ alkyl acetate = ◊.

It may be noted from these figures that:
The introduction of cobalt to the ruthenium-manganese catalyst increases both the total alcohol + alkyl acetate productivity and the total $C_1$–$C_4$ alcohol productivity substantially.

What is claimed is:
1. A process for making $C_1$–$C_4$ alkanols which comprises contacting a mixture of synthesis gas (e.g. carbon monoxide and hydrogen) at a pressure of at least 30 atm and at a temperature of at least 150° C. with a trimetallic catalyst system comprising a ruthenium-containing compound, a cobalt-containing compound and a manganese-containing compound dispersed in a low melting quaternary phosphonium salt wherein there is one or more of the following: improved total $C_1$–$C_4$ alcohol + $C_1$–$C_4$ alkyl acetate productivity, improved selectivity for total $C_1$–$C_4$ alkanols, improved ethanol productivity, and improved $C_1$–$C_4$ alcohol to $C_1$–$C_4$ alkyl acetate molar ratio.

2. The process of claim 1 wherein the process is conducted at a pressure of about 130 atm to about 600 atm.

3. The process of claim 1 wherein the process is conducted at a temperature of about 150° to about 350° C.

4. The process of claim 1 wherein the quaternary salt or base has a melting point less than about 180° C.

5. The process of claim 1 wherein the quaternary salt s a tetraalkylphosphonium salt.

6. The process of claim 5 wherein the alkyl groups contain 1-6 carbon atoms.

7. The process of claim 1 wherein the quaternary is a mixed alkylaryl phosphonium quaternary.

8. The process of claim 1 wherein the quaternary salt is tetrabutylphosphonium salt.

9. The process of claim 8 wherein the tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

10. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl derivatives.

11. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

12. The process of claim 1 wherein said ruthenium-containing compound is triruthenium dodecacarbonyl.

13. The process of claim 1 wherein the cobalt-containing compound is selected from the group consisting of one or more oxides of cobalt, cobalt salts of an organic carboxylic acid, cobalt complexes with carbonyl-containing ligands, and cobalt carbonyl and hydrocarbonyl derivatives.

14. The process of claim 1 wherein the cobalt-containing compound is selected from the group consisting of dicobalt octacarbonyl, cobalt(III) acetylacetonate, cobalt(II) acetate, cobalt(II) propionate and cobalt(II) acetylacetonate.

15. The process of claim 14 wherein the cobalt-containing compound is dicobalt octacarbonyl.

16. The process of claim 1 wherein the manganese-containing compound is selected from the group consisting of one or more oxides of manganese, manganese salts of an organic carboxylic acid, manganese complexes with carbonyl-containing ligands and manganese carbonyl and hydrocarbonyl derivatives.

17. The process of claim 16 wherein the manganese-containing compound is selected from the group consisting of manganese(II) carbonate, manganese(III) acetylacetonate, dimanganese decacarbonyl and manganese(II) acetate.

18. The process of claim 17 wherein the manganese-containing compound is dimanganese decacarbonyl.

19. The process of claim 1 wherein the ruthenium-containing compound is a ruthenium carbonyl, the cobalt-containing compound is a cobalt carbonyl and the manganese-containing compound is a manganese carbonyl.

* * * * *